US005332427A

United States Patent [19]

Hayashi et al.

[11] Patent Number: 5,332,427

[45] Date of Patent: Jul. 26, 1994

[54] WOOD PRESERVATIVES

[75] Inventors: Yoko Hayashi, Toyonaka; Takaaki Itoh, Nishinomiya, both of Japan

[73] Assignee: Sumitomo Chemical Company, Limited, Osaka, Japan

[21] Appl. No.: 943,019

[22] Filed: Sep. 10, 1992

[30] Foreign Application Priority Data

Sep. 13, 1991 [JP] Japan ................................ 3-234633

[51] Int. Cl.$^{5}$ ...................... C09D 5/14; C07D 249/08

[52] U.S. Cl. .............................. 106/18.32; 106/18.35; 427/397; 427/421; 427/440; 504/181; 504/274; 514/383; 514/396; 514/397; 514/399; 548/262.2; 548/267.2; 548/268.4; 548/341.1

[58] Field of Search .......................... 106/18.32, 18.35; 504/181, 274; 514/383, 396, 397, 399; 548/262.2, 267.2, 268.4, 341.1; 427/421, 440, 397

[56] References Cited

U.S. PATENT DOCUMENTS

| | | | |
|---|---|---|---|
| 4,203,995 | 5/1980 | Funaki et al. | 514/383 |
| 4,435,203 | 3/1984 | Funaki et al. | 504/181 |
| 4,542,146 | 9/1985 | Gestel et al. | 514/383 |
| 4,554,007 | 11/1985 | Funaki et al. | 504/181 |
| 5,013,748 | 5/1991 | Radtke et al. | 514/383 |
| 5,091,401 | 2/1992 | Scele et al. | 514/383 |

FOREIGN PATENT DOCUMENTS

| | | |
|---|---|---|
| 0038109 | 10/1981 | European Pat. Off. . |
| 0054431 | 6/1982 | European Pat. Off. . |
| 0148526 | 7/1985 | European Pat. Off. . |
| 0341954 | 11/1989 | European Pat. Off. . |
| 0407854 | 1/1991 | European Pat. Off. . |
| 2588724 | 4/1987 | France . |
| 2169804 | 7/1986 | United Kingdom . |

OTHER PUBLICATIONS

*Ann. appl. Biol.* (1983), 102, 435–453, C. Mercer et al.: "Chemical treatments for control of decay in pruning wounds".

*Primary Examiner*—Anthony Green
*Attorney, Agent, or Firm*—Stevens, Davis, Miller & Mosher

[57] ABSTRACT

A wood preservative comprising a styryl triazole derivative of the formula [I]

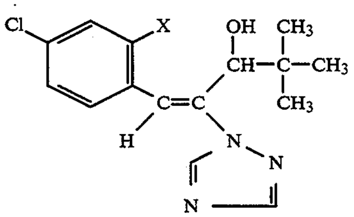

[I]

wherein X represents chlorine or hydrogen as an active ingredient. The present wood preservative has a wood-preserving efficacy equivalent to and remarkably improved light resistance as compared with a conventional organic iodine compound slightly inferior in light resistance, and therefore, exhibits a stabilized wood-preservating efficacy without causing discoloration even under irradiation with light.

4 Claims, No Drawings

WOOD PRESERVATIVES

The present invention relates to a wood preservative and a method for preservating wood using the same.

Among wood preservatives, heretofore, an organic iodine compound has been widely used especially for wooden surface treatment.

However, there has been a problem that said compound is easily decomposed by light and heat to discolor to pale yellow to yellowish brown.

Hence, the present inventors have made extensive research on developing a wood preservative whose wood-preservating efficacy is not inferior to that of conventional wood preservatives and which is not discolored by heat and light, and as a result, they have found a compound capable of achieving the purpose.

According to the present invention, there is provided a wood preservative comprising a styryl triazole derivative of the formula [I]

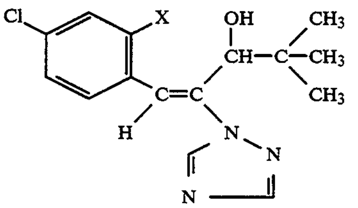

[I]

wherein X represents chlorine or hydrogen (referred to hereinafter as compound [I]) as an active ingredient and a method for preservating wood using the same.

Examples of compound [I] are listed below, (1) (−)-(E)-1-(2,4-dichlorophenyl)-4,4-dimethyl-2-(1,2,4-triazol-1-yl)-1-penten-3-ol (2) (−)-(E)-1-(4-chlorophenyl)-4,4-dimethyl-2-(1,2,4-triazol-1-yl)-1-penten-3-ol (3) (±)-(E)-1-(2,4-dichlorophenyl)-4,4-dimethyl-2-(1,2,4-triazol-1-yl)-1-penten-3-ol (4) (±)-(E)-1-(4-chlorophenyl)-4,4-dimethyl-2(1,2,4-triazol-1-yl)-1-penten-3-ol Compound [I] can be produced according to the method described in the specification of U.S. Pat. No. 4,554,007 or U.S. Pat. No. 4,435,203.

In the application of the present wood preservative, compound [I] may be used as it is without adding any other ingredient. However, compound [I] is usually mixed with an inert carrier such as a solid carrier, a liquid carrier or a gaseous carrier and, if necessary, a surface active agent, a stabilizer and other auxiliaries for formulation are added to the mixture, after which the resulting mixture is formulated into an oil formulation; an emulsifiable concentrate; a wettable powder; a flowable formulation such as an in-water suspension, an in-water emulsion, etc.; a dust; an aerosol; or the like. The formulation thus obtained is used.

These formulations contain compound [I] as an active ingredient in an amount of usually 0.01–95% by weight, preferably 0.2–60% by weight.

The solid carrier used in the formulation includes, for example, fine powders and granules of clays (kaolin clay, diatomaceous earth, synthetic hydrated silicon dioxide, bentonite, fubasamiclay, terra alba, etc.), talcs, ceramics, other inorganic minerals (serite, quartz, sulfur, activated charcoal, calcium carbonate, hydrated silica, etc.) and the like. The liquid carrier includes, for example, water, alcohols [ethanol, isopropanol, 3-methyl-3-methoxybutanol, glycols (polyethylene glycol, polypropylene glycol, etc.)], ketones (acetone, methyl ethyl ketone, etc.), aromatic hydrocarbons (benzene, toluene, xylene, alkylbenzene, methylnaphthalene, etc.), aliphatic hydrocarbons (hexane, cyclohexane, kerosene, light oil, etc.), esters [ethyl acetate, butyl acetate, higher fatty acid esters (isopropyl myristate, etc.), 3-methyl-3-methoxybutyl acetate, etc.], nitriles (acetonitrile, isobutyronitrile, etc.), ethers (diisopropyl ether, dioxane, etc.), acid amides (N,N-dimethylformamide, N,N-dimethylacetoamide, etc.), halogenated hydrocarbons (dichloromethane, trichloroethane, carbon tetrachloride, etc.), dimethylsulfoxide, vegetable oils (soybean oil, cottonseed oil, etc.) and the like (these can also be used in admixture). The gaseous carrier, namely, proplant, includes, for example, fron gas, butane gas, LPG (liquefied petroleum gas), dimethyl ether, carbon dioxide, etc.

The surface active agent includes, for example, alkylsulfuric esters, alkylsulfonic acid salts and alkylarylsulfonic acid salts, alkyl aryl ethers and polyoxyethylenated products thereof, polyethylene glycol ethers, polyhydric alcohol esters, sugar alcohol derivatives, etc.

The auxiliaries for formulation are a sticking agent, a dispersing agent, etc. and include, for example, casein, gelatin, polysaccharides (starch, gum arabic, cellulose derivatives, alginic acid, etc.), lignin derivatives, bentonite, sugars, synthetic water-soluble polymers (polyvinyl alcohols, polyvinyl pyrrolidone, polyacrylic acids, etc.), and the stabilizer includes, for example, PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), a vegetable oil, a mineral oil, a surface active agent, a fatty acid and its ester, etc.

The flowable formulation (an in-water suspension or an in-water emulsion) is generally obtained by micro-dispersing 1–75% by weight of compound [I] in water containing 0.5–15% by weight of a dispersing agent, 0.1–10% by weight of a suspension adjuvant (for example, a protective colloid and a thixotropy-imparting compound), 0.1–10% by weight of adequate auxiliaries (for example, an antifoaming agent, a rust inhibitor, a stabilizer, a spreader, a penetrant auxiliary, an antifreezing agent, a bactericide, a fungicide, etc.). Compound [I] can also be formulated into an in-oil suspension by using, instead of water, an oil in which compound [I] scarcely dissolves. As the protective colloid, there is used, for example, gelanin, casein, gums, cellulose ether, polyvinylalcohol or the like. As the thixotropy-imparting compound, there is used, for example, bentonite, aluminium magnesium silicate, xanthane gum, polyacrylic acid, or the like.

The formulations thus obtained are used as they are or after diluting them with water, etc. Said formulations can be applied in admixture with or separately from and simultaneously with other wood preservatives, insecticides, acaricides, termiticides (controlling agents for termites), fungicides or synergists.

The termiticides to be used include chlorpyrifos, phoxim, fenitrothion, fenobucarb, permethrin, tralomethrin, cypermethrin, deltamethrin, cyfluthrin and fenvalerate.

The oil formulation, dust, granule and aerosol are applied as they are and the emulsifiable concentrate, wettable powder and flowable formulation are applied after diluting them with water to 0.01–10% by weight, preferably 0.05–5% by weight.

The amount and concentration of the active ingredient applied are varied depending on the kind of formulation, the application time, the application place, the application method, the kind of wood rotting fungi and the degree of wooden damage, etc. and they can be increased or decreased regardless of the above range.

The present wood preservative is applied to wood (including bamboos herein) by a surface treatment means such as dipping, spraying, coating, etc., or a means such as injection under pressure or injection under vacuum, or applied in admixture with an adhesive for plywood to prepare a plywood or especially applied to construction materials, to act as a controlling agent for wood rotting fungi.

The wood that is the object for controlling wood rotting fungi includes, for example, Fagaceae such as Japanese beech, Taxodiaceae such as Japanese cedar, Pinaceae such as Japanese red pine and the like. The adhesive for plywoods includes, for example, a phenol resin, a melamine resin, a urea resin, etc.

The wood rotting fungi that can be controlled by the present wood preservative, are for example, *Coriolus versicolor, Tyromyces palustris, Serpula lacrymans, Paxillus panuoides, Coniophora puteana, Gloeophyllum sepiarium, Gloeophyllum trabeum, Antrodia xantha, Lentinus lepideus, Antrodia sinuosa, Schiozophyllum commune, Pycnoporus coccineus,* etc.

The present wood preservative is used preferably as a wooden surface treating agent and, in this case, usually used in the form of an oil formulation in an amount of 50–200 g of the oil formulation per $m^2$ of surface area of wood and in an amount of 0.1–10 g of the active ingredient per $m^2$ of surface area of wood.

The present wood preservative has a wood-preserving efficacy equivalent to and remarkably improved light resistance as compared with a conventional organic iodine compound slightly inferior in light resistance, and therefore, can exhibit a stabilized wood-preservating efficacy without causing discoloration even under irradiation with light.

The present invention is specifically explained below referring to Examples. However, the present invention is not limited thereto. In the Examples, parts and % are by weight unless otherwise specified.

First of all, formulation examples are shown.

FORMULATION EXAMPLE 1 (Oil Formulation)

With 1 part of compound (1) or (2) were mixed 0.2 part of (3-phenoxyphenyl)methyl 3-(2,2-dichloroethenyl)-2,2-dimethylcyclopropanecarboxylate (common name: permethrin), 1.5 parts of bis(2,3,3,3-tetrachloropropyl) ether (S-421), 10 parts of 3-methyl-3-methoxybutanol (Sorfit: manufactured by Kuraray Co., Ltd.) any 87.3 parts of kerosene to prepare a 1% oil formulation.

FORMULATION EXAMPLE 2 (Emulsion)

With 2 parts of compound (1) or (2) were mixed 88 parts of xylene and 10 parts of Sorpol SM 200 (manufactured by Toho Chemical Co., Ltd.) to prepare a 2% emulsifiable concentrate.

Next, test examples are shown. Compounds (A), (B) and (C) (all of them are commercially available) used for comparison are shown in Table 1.

TABLE 1

| Compound | Compound name |
|---|---|
| (A) | 3-Bromo-2,3-diiodo-2-propenylethyl carbonate |
| (B) | 3-Iodo-2-propenylbutyl carbamate |
| (C) | 4-Chlorophenyl-3-iodopropargyl formal |

TEST EXAMPLE 1

A 1% oil formulation of each of the test compounds shown in Table 2 was prepared according to Formulation Example 1. The oil formulation was coated on a filter paper having a diameter of 5.5 cm in an amount of 100 ml of the oil formulation per $m^2$ of the filter paper and the filter paper was air-dried. The filter paper thus prepared was subjected to irradiation with light of 6000–7000 lux for 5 minutes and then, taken out, after which the degree of discoloration (coloration) was observed. The degree of discoloration (coloration) was determined based on the following standard.

No discoloration (coloration): −

Slight discoloration (coloration): +

Prominent discoloration (coloration): ++

The results are shown in Table 2.

TABLE 2

| Test compound | Degree of discoloration (coloration) |
|---|---|
| Compound (1) | − |
| Compound (2) | − |
| Compound (A) | ++ |
| Compound (B) | + |
| Compound (C) | ++ |

TEST EXAMPLE 2

Each of the test compounds shown in Tables 3 and 4 was dissolved in a definite amount of dimethylsulfoxide to prepare a 1% W/V solution. A definite amount of the resulting formulation was added to a potato dextrose agar medium just after sterilization (using a moist heat sterilizer) and about 20 cc of the mixture was poured into a Petri dish of 9 cm in diameter and the Petri dish was placed at room temperature. After the medium was solidified, mycelium from a colony of *Coriolus versicolor* or *Tyromyces palustris* cultured previously was punched with a cork borer of 5 mm in diameter and the mycelium was inoculated at the center of the test medium. Four days after the inoculation, the diameter of colony extended from the inoculation point was measured and the percentage of mycelium growth inhibition was calculated according to the following equation:

$$\text{Percentage of mycelium growth inhibition (\%)} = \frac{\text{Diameter of colony in untreated plot} - \text{Diameter of colony in treated plot}}{\text{Diameter of colony in untreated plot}} \times 100$$

The results are shown in Tables 3 and 4.

TABLE 3

Percentage of growth inhibition for *Coriolus versicolor*

| Test compound | Concentration (ppm) 4 | 2 | 1 |
|---|---|---|---|
| Compound (1) | 98.3 | 93.9 | 86.1 |
| Compound (2) | 93.9 | 87.2 | 85.3 |
| Compound (A) | 72.8 | 41.7 | 20.0 |
| Compound (B) | 100 | 91.9 | 81.3 |

TABLE 3-continued

| Percentage of growth inhibition for *Coriolus versicolor* | | | |
|---|---|---|---|
| | Concentration (ppm) | | |
| Test compound | 4 | 2 | 1 |
| Compound (C) | 97.9 | 88.7 | 68.2 |

TABLE 4

| Percentage of growth inhibition for *Tyromyces palustris* | | | |
|---|---|---|---|
| | Concentration (ppm) | | |
| Test compound | 4 | 2 | 1 |
| Compound (1) | 95.6 | 93.0 | 79.1 |
| Compound (2) | 100 | 98.8 | 94.6 |
| Compound (A) | 63.3 | 43.0 | 26.6 |
| Compound (B) | 100 | 88.7 | 80.5 |
| Compound (C) | 100 | 98.6 | 77.0 |

TEST EXAMPLE 3

An oil formulation of each of the test compounds shown in Table 5 was prepared according to Formulation Example 1 and was tested based on the test method of Japan Wood Preservation Association. The summary of the test method is as follows:

The cut end surfaces of a wooden piece of Japanese beech or Japanese cedar (thickness: 5 mm, width: 20 mm, length: 40 mm; the surface of 40×20 mm is of straight grain) were sealed with an epoxy resin and the wooden piece was impregnated with the oil formulation ($110\pm10$ g/$m^2$ surface area), and thereafter air-dried for 20 days to prepare a test specimen. The test specimen was dipped in still water [water:wooden piece=10:1 (volume ratio)] at 25°±3° C. for 5 hours, and then the water was volatilized at 40±2° C. for 19 hours. This weather resistance operation was repeated 30 times. The test specimen after the weather resistance operation was dried at 60°±2° C. for 48 hours and then placed in a desicator for about 30 minutes, after which the weight ($W_3$) of the test specimen was measured. The test described above was repeated for 9 wooden pieces. The test specimen was sterilized and then, placed in a culture vial in which wood rotting fungi (*Coriolus versicolor*/Japanese beech, *Tyromyces palustris*/Japanese cedar) were being cultured, in which cultivation was effected at 26°±2° C. at a humidity of 80% for 8 weeks. After 8 weeks, the test specimen was taken out of the culture vial and the mycelium and other extraneous matters were removed therefrom, after which the test specimen was dried at 60°±2° C. for 48 hours and placed in a desicator for about 30 minutes. Thereafter, the weight ($W_4$) of the test specimen was measured. The weight reduction percentage was calculated according to the following equation:

$$\text{Weight reduction percentage (\%)} = \frac{(W_3 - W_4)}{W_3} \times 100$$

The results obtained are shown in Table 5.

TABLE 5

| Test compound | Concentration (%) | Average weight reduction percentage (%) *Coriolus versicolor*/ Japanese beech | *Tyromyces palustris*/ Japanese cedar |
|---|---|---|---|
| Compound (1) | 0.5 | 0.70 | 0.25 |
| Compound (1) | 1.0 | 0.64 | 0.19 |
| Compound (A) | 1.0 | 3.9 | 3.1 |
| Compound (B) | 1.0 | 7.6 | 0.78 |
| Compound (C) | 1.0 | 1.1 | 0.34 |
| Untreated | — | 42 | 36 |

What is claimed is:

1. A method of preserving wood comprising applying to a wooden surface, a fungicidally effective amount of a wood preservative comprising a styryl triazole derivative of the formula (I)

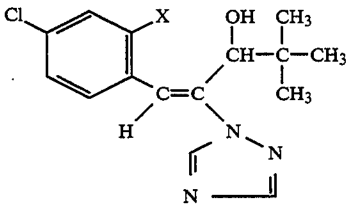

(I)

wherein X represents chlorine or hydrogen as an active ingredient and an inert carrier;
wherein the wood preservative is in the form of an oil formulation;
wherein the wood preservative is applied to the wooden surface in an amount of 50–200 g of the oil formulation per $m^2$ of the surface area of wood and in an amount of 0.1–10 g of the active ingredient per $m^2$ of surface area of wood.

2. The method for preservating wood according to claim 1, wherein the content of the active ingredient is 0.01–95% by weight.

3. A method for controlling wood rotting fungi which comprises applying a fungicidally effective amount of a styryl triazole derivative of the formula (I)

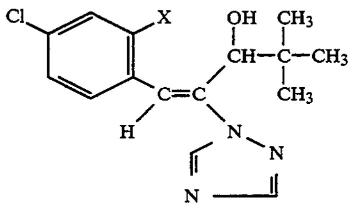

(I)

wherein X represents chlorine or hydrogen, to wood,
wherein the applying of the styryl triazole derivative is in an antifungally effective amount which is effective against at least one fungus selected from the group consisting of *Coriolus versicolor, Tyrtomyces palustris, Serpula lacrymans, Paxillus panuoides, Coniophora puteana, Gloeophyllum sepiarium, Gloeophyllum trabeum, Antrodia xantha, Lentinus lepideus, Antrodia sinuosa, Schiozophyllum commune* and *Pycnoporus coccineus.*

4. The method for controlling wood rotting fungi according to claim 3, wherein the applying of the styryl triazole derivative is in an anti-fungally effective amount which is effective against at least one fungus selected from the group consisting of *Coriolus versicolor* and *Tyromyces palustris.*

* * * * *